United States Patent
Candau

[11] Patent Number: 6,159,456
[45] Date of Patent: Dec. 12, 2000

[54] PHOTOPROTECTIVE/COSMETIC COMPOSITIONS COMPRISING CAMPHORSULFONIC ACID AND BISRESORCINYLTRIAZINE SUNSCREENS

[75] Inventor: Didier Candau, Bievres, France

[73] Assignee: Societe L'Oreal S.A., Paris, France

[21] Appl. No.: 09/503,940

[22] Filed: Feb. 14, 2000

[51] Int. Cl.$^7$ ............... A61K 7/42; A61K 7/44; A61K 7/00
[52] U.S. Cl. ............... 424/59; 424/60; 424/400; 424/401
[58] Field of Search ............... 424/59, 60, 400, 424/401

[56] References Cited
FOREIGN PATENT DOCUMENTS

| | | |
|---|---|---|
| 0 685 224 A1 | 12/1995 | European Pat. Off. . |
| 0 878 469 A1 | 11/1998 | European Pat. Off. . |
| 196 45 317 A1 | 5/1998 | Germany . |
| WO 98/22447 | 5/1998 | WIPO . |
| WO 99/08653 | 2/1999 | WIPO . |

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for the synergistically enhanced photoprotection of human skin and/or hair against the damaging effects of UV-irradiation, particularly solar radiation, comprise synergistically UV-photoprotecting effective amounts of each of (i) benzene-1,4-di(3-methylidene-10-camphorsulfonic acid, or partially or completely neutralized form thereof, and (ii) at least one bisresorcinyltriazine compound, formulated into a topically applicable, cosmetically acceptable vehicle, diluent or carrier therefor.

25 Claims, No Drawings

PHOTOPROTECTIVE/COSMETIC COMPOSITIONS COMPRISING CAMPHORSULFONIC ACID AND BISRESORCINYLTRIAZINE SUNSCREENS

CROSS-REFERENCE TO PRIORITY APPLICATION

This application claims priority under 35 U.S.C. §119 of FR-99/01730, filed Feb. 12, 1999, hereby expressly incorporated by reference.

BACKGROUND OF THE INVENTION

1. Technical Field of the Invention

The present invention relates to novel cosmetic compositions for topical application, for the photoprotection of the skin and/or hair against ultraviolet radiation (such compositions hereinafter simply designated "antisun," "sunscreen" or "photoprotective" compositions) and to the use of same for the cosmetic applications indicated above.

This invention more especially relates to the aforesaid sunscreen/cosmetic compositions comprising, formulated into a cosmetically acceptable vehicle, diluent or carrier therfor, a combination of at least two specific screening agents, namely, on the one hand, benzene-1,4-di(3-methylidene-10-camphorsulfonic acid) and, on the other, a specific bisresorcinyltriazine compound or salt thereof, these two screening agents being present in proportions suitable for eliciting a synergistic effect with regard to the protection factors conferred.

2. Description of the Prior Art

It is known to this art that light radiation with wavelengths of from 280 nm to 400 nm promotes tanning of the human epidermis and that irradiation with wavelengths of from 280 and 320 nm, i.e., UV-B radiation, causes erythemas and skin burns which may be harmful to the development of natural tanning; this UV-B radiation must therefore be screened from the skin.

It is also known to this art that UV-A radiation, with wavelengths of from 320 to 400 nm, which causes tanning of the skin, can also adversely affect it, in particular in the case of sensitive skin or of skin continually exposed to solar radiation. UV-A rays cause, in particular, a loss in the elasticity of the skin and the appearance of wrinkles, resulting in premature aging. Such irradiation promotes the triggering of the erythemal reaction or accentuates this reaction in certain individuals and can even be the source of phototoxic or photoallergic reactions. Thus, it is also desirable to screen out UV-A radiation.

A wide variety of cosmetic compositions for the photoprotection (UV-A and/or UV-B) of human skin are known to this art.

These photoprotective/sunscreen compositions are typically emulsions of oil-in-water type (namely, a cosmetically acceptable vehicle, diluent or carrier comprising a continuous aqueous dispersing phase and a non-continuous oily dispersed phase) which contains, in various concentrations, one or more conventional lipophilic and/or hydrophilic organic screening agents capable of selectively absorbing harmful UV radiation. These screening agents (and the amounts thereof) are selected as a function of the desired protection factor (the protection factor (PF) being expressed mathematically by the ratio of the irradiation time required to attain the erythemogenic threshold with the UV screening agent to the time required to attain the erythemogenic threshold without UV screening agent).

SUMMARY OF THE INVENTION

It has now surprisingly and unexpectedly been determined that the combination of two specific sunscreen compounds already per se known to this art provides synergistically active sunscreen compositions exhibiting markedly improved protection factors, protection factors which are much higher than those which can be obtained either with one or the other of the screening agents used alone.

Briefly, the present invention features novel cosmetic compositions, in particular photoprotective/sunscreen compositions, comprising, in a cosmetically acceptable vehicle, diluent or carrier,(i) benzene-1,4-di(3-methylidene-10-camphorsulfonic acid), optionally in a partially or completely neutralized state, as a first photoprotecting agent, and (ii) at least one specific bisresorcinyltriazine compound as a second photoprotecting agent, the said first and second screening agents advantageously being formulated into the subject compositions in a proportion eliciting a synergistic effect with regard to the sun protection factors conferred.

The present invention also features the use of the subject compositions as or in the production of cosmetic compositions suited for the protection of the skin and/or hair against the deleterious effects of ultraviolet radiation, in particular solar radiation.

This invention thus also features a cosmetic regime/regimen for the photoprotection of skin and/or hair against the damaging effects of ultraviolet radiation, in particular solar radiation, which essentially entails topically applying onto the skin/hair a photoprotecting effective amount of a composition in accordance herewith.

DETAILED DESCRIPTION OF BEST MODE AND SPECIFIC/PREFERRED EMBODIMENTS OF THE INVENTION

More particularly according to the present invention, benzene-1,4-di(3-methylidene-10-camphorsulfonic acid) and its various salts, described in particular in FR-A-2,528,420 and FR-A-2,639,347, are screening agents per se already known (so-called broad spectrum screening agents), capable of absorbing ultraviolet rays having wavelengths of from 280 to 400 nm, with absorption maxima of from 320 to 400 nm, in particular in the vicinity of 345 nm.

These screening agents have the following structural formula (I):

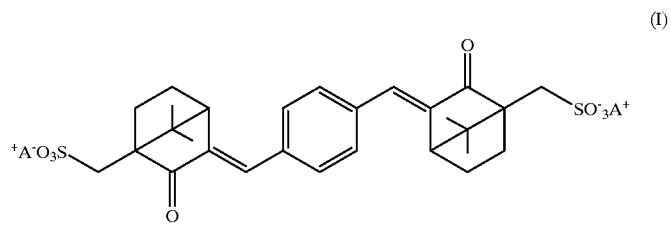

in which A is a hydrogen atom, an alkali metal or an $NH(R)_3^+$ radical wherein the R radicals, which may be identical or different, are each a hydrogen atom, a $C_1$–$C_4$ alkyl or hydroxyalkyl radical, or an $M^{n+}/n$ group, wherein $M^{n+}$ is a polyvalent metal cation in which n is equal to 2, 3 or 4, with $M^{n+}$ preferably being a metal cation selected from among $Ca^{2+}$, $Zn^{2+}$, $Mg^{2+}$, $Ba^{2+}$, $Al^{3+}$ and $Zr^{4+}$. It will be appreciated that the compounds of formula (I) also comprehend the "cis-trans" isomer about one or more double bond(s) and that all such isomers are within the scope of the present invention.

The benzene-1,4-di(3-methylidene-10-camphorsulfonic acid) and/or one of its various salts is advantageously present in the screening compositions according to the invention at a total concentration ranging from 0.1% to 15% by weight, approximately, and preferably from 0.2% to 10% by weight, approximately, with respect to the total weight of the composition.

The bisresorcinyltriazine compounds in accordance with the present invention have the following structural formula (II):

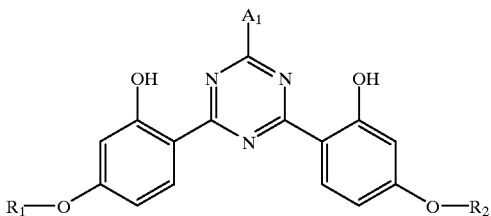

(II)

in which (i) the $R_1$ and $R_2$ radicals, which may be identical or different, are each a $C_3$–$C_{18}$ alkyl radical, a $C_2$–$C_{18}$ alkenyl radical, or a residue of formula —$CH_2$—$CH(OH)$—$CH_2$—$OT_1$ wherein $T_1$ is a hydrogen atom or a $C_1$–$C_8$ alkyl radical; (ii) with the proviso that the $R_1$ and $R_2$ radicals, which again may be identical or different, can also be a residue having the following formula (1):

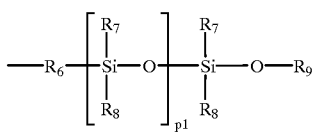

(1)

in which $R_6$ is a covalent bond, a linear or branched $C_1$–$C_4$ alkyl radical, or a residue of formula —$C_{m1}H_{2m1}$— or —$C_{m1}H_{2m1}$—O— wherein $m_1$ is a number ranging from 1 to 4; $p_1$ is a number ranging from 0 to 5; and the $R_7$, $R_8$ and $R_9$ radicals, which may be identical or different, are each a $C_1$–$C_{18}$ alkyl radical, a $C_1$–$C_{18}$ alkoxy radical, or a residue having the formula:

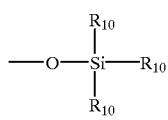

(2)

wherein $R_{10}$ is a $C_1$–$C_5$ alkyl radical; and $A_1$ is a residue having one of the following formulae:

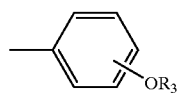

(3)

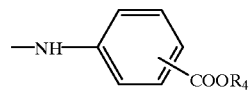

(4)

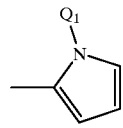

(5)

in which $R_3$ is a hydrogen atom, a $C_1$–$C_{10}$ alkyl radical, a radical of formula —$(CH_2CHR_5$—$O)_{n1}R_4$ wherein $n_1$ is a number ranging from 1 to 16 and $R_5$ is hydrogen or a methyl radical, or a residue having the formula —$CH_2$—$CH(OH)$—$CH_2OT_1$ wherein $T_1$ is as defined above; $R_4$ is hydrogen, a metal cation M, a $C_1$–$C_5$ alkyl radical or a residue of formula —$(CH_2)_{m2}$—$OT_1$, wherein $m_2$ is a number ranging from 1 to 4 and $T_1$ is as defined above; and $Q_1$ is a $C_1$–$C_{18}$ alkyl radical.

In the formulae (II) and (1) to (5) described above:
(a) the alkyl radicals may be linear or branched and advantageously are selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl or octadecyl radicals;
(b) the alkenyl radicals are advantageously selected, for example, from among allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isodedecenyl or n-octadec-4-enyl radicals;
(c) the alkoxy radicals are linear or branched and advantageously are selected, for example, from among methoxy, ethoxy, n-propoxy, isopropoxy, n-butoxy, sec-butoxy, tert-butoxy, amyloxy, isoamyloxy or tert-amyloxy radicals;
(d) the mono- or di($C_1$–$C_5$)alkylamino radicals are advantageously selected, for example, from among methylamino, ethylamino, propylamino, n-butylamino, sec-butylamino, tert-butylamino, pentylamino, dimethylamino, diethylamino, dibutylamino or methylethylamino radicals;
(e) the metal cations M are alkali metal, alkaline earth metal, or metal cations advantageously selected, for example, from among lithium, potassium, sodium, calcium, magnesium, copper and zinc.

The bisresorcinyltriazine compounds of formula (II) of the invention are screening agents also per se known to this art. They are described and prepared according to the syntheses illustrated in EP-A-0,775,698, hereby expressly incorporated by reference.

Exemplary compounds of formula (II) include:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethyloxycarbonyl)phenylamino]-1,3,5-triazine;

2,4-bis{[4-(tris(trimethylsiloxy)silylpropyloxy)-2-hydroxy]phenyl}-6-(4-methoxyphenyl)-1,3,5-triazine;

2,4-bis{[4-(2"-methylpropenyloxy)-2-hydroxy]phenyl}-6-(4-methoxyphenyl)-1,3,5-triazine;

2,4-bis{[4-(1',1',1',3',5',5',5'-heptamethyltri-siloxy-2"-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-(ethoxycarbonyl)phenylamino]-1,3,5-triazine;

2,4-bis{[4-(2-ethylhexyloxy)-2-hydroxy]phenyl}-6-(1-methylpyrrol-2-yl)-1,3,5-triazine.

The bisresorcinyltriazine compounds which are more particularly preferred according to the invention are selected from among:

2,4-bis{[4-(2-ethylhexyloxy)-2-hydroxy]phenyl}-6-(4-methoxyphenyl)-1,3,5-triazine;

2,4-bis{[4-(tris(trimethylsiloxy)silylpropyloxy)-2-hydroxy]phenyl}-6-(4-methoxyphenyl)-1,3,5-triazine;

2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

The organic screening agent or agents of the bisresorcinyltriazine compound type of formula (II) are generally formulated into the screening compositions according to the invention at a total concentration ranging from 0.1% to 15% by weight, approximately, and preferably from 0.2% to 10% by weight, approximately, with respect to the total weight of the composition.

As indicated above, in a characteristic embodiment of the present invention, the subject two compounds are each present in the final composition in respective proportions such that a substantial and significant synergistic effect is obtained with regard to the protection factor conferred by the resulting combination.

In addition and generally, it should be noted that the concentrations and ratios of the compounds of formula (I) and the compounds of formula (II) are selected such that the sun protection factor of the final composition is preferably at least 2.

In another preferred embodiment of the present invention, the cosmetically acceptable medium (vehicle, diluent or carrier) in which the various organic screening agents of formula (I) and of formula (II) are present is an emulsion of oil-in-water type.

The sunscreen/antisun cosmetic compositions according to the invention can, of course, contain one or more additional hydrophilic or lipophilic sunscreens which are active in the UV-A and/or UV-B regions (absorbers), other than the two screening agents indicated above. These additional screening agents are advantageously selected from among cinnamic derivatives, salicylic derivatives, camphor derivatives, triazine derivatives other than those described above, such as those described in EP-863,145, EP-517,104, EP-570,838 and EP-796,851, benzophenone derivatives, dibenzoylmethane derivatives, β-β-diphenylacrylate derivatives, benzimidazole derivatives, p-aminobenzoic acid derivatives, or screening polymers and screening silicones, such as those described in WO-93/04665.

Exemplary such additional sunscreens which are active in the UV-A and/or UV-B ranges include:

p-aminobenzoic acid;

oxyethylenated (25 mol) p-aminobenzoate;

2-ethylhexyl p-dimethylaminobenzoate;

N-oxypropylenated ethyl p-aminobenzoate;

glycerol p-aminobenzoate;

homomenthyl salicylate;

2-ethylhexyl salicylate;

triethanolamine salicylate;

4-isopropylbenzyl salicylate;

4-tert-butyl-4'-methoxydibenzoylmethane;

4-isopropyldibenzoylmethane;

2-ethylhexyl 4-methoxycinnamate;

methyl diisopropylcinnamate;

isoamyl 4-methoxycinnamate;

diethanolamine 4-methoxycinnamate;

menthyl anthranilate;

2-ethylhexyl 2-cyano-3,3-diphenylacrylate;

ethyl 2-cyano-3,3-diphenylacrylate;

2-phenylbenzimidazole-5-sulfonic acid and its salts;

3-(4'-trimethylammonio)benzylidenebornan-2-one methyl sulfate;

2-hydroxy-4-methoxybenzophenone;

2-hydroxy-4-methoxybenzophenone-5-sulfonate;

2,4-dihydroxybenzophenone;

2,2',4,4'-tetrahydroxybenzophenone;

2,2'-dihydroxy-4,4'-dimethoxybenzophenone;

2-hydroxy-4-(n-octoxy)benzophenone;

2-hydroxy-4-methoxy-4'-methylbenzophenone;

urocanic acid;

α-(2-oxoborn-3-ylidene)toluene-4-sulfonic acid and its salts;

3-(4'-sulfobenzylidene)bornan-2-one and its salts;

3-(4'-methylbenzylidene)-d,l-camphor;

3-benzylidene-d,l-camphor;

2,4,6-tris[p-(2'-ethylhexyl-1'-oxycarbonyl)anilino]-1,3,5-triazine;

2-[p-(tert-butylamido)anilino]-4,6-bis[(p-(2'-ethyl-hexyl-1'-oxycarbonyl)anilino]-1,3,5-triazine;

1,4-bis(benzimidazolyl)phenylene-3,3',5,5'-tetrasulfonic acid and its salts;

the polymer of N-[(2- and 4-)[(2-oxoborn-3-ylidene)-methyl]benzyl]acrylamide;

drometrizole trisiloxane (INCI designation);

polyorganosiloxanes comprising a malonate functional group.

The compositions according to the invention can also contain active agents for the artificial tanning and/or browning of the skin (self-tanning agents), such as, for example, dihydroxyacetone (DHA).

The cosmetic compositions of this invention can also contain pigments or alternatively nanopigments (mean size of the primary particles: generally ranging from 5 nm to 100 nm, preferably from 10 to 50 nm), comprising metal oxides which are coated or uncoated, such as, for example, titanium dioxide (amorphous or crystallized in the rutile and/or anatase form), iron oxide, zinc oxide, zirconium oxide or cerium oxide nanopigments which are all photoprotective agents well known per se which act by physically blocking (reflection and/or scattering) UV radiation. Furthermore, alumina and/or aluminum stearate are conventional coating agents. Such coated or uncoated metal oxide nanopigments are described, in particular, in EP-A-0,518,772 and EP-A-0,518,773.

The compositions of the invention can additionally contain conventional cosmetic additives and adjuvants selected, in particular, from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, polymers, propellants, basifying or acidifying agents, dyes, colorants, or any other ingredient commonly formulated into cosmetics, in particular in the production of antisun/sunscreen compositions formulated as emulsions.

Exemplary fatty substances include oils or waxes or their mixtures and they also comprise fatty acids, fatty alcohols and fatty acid esters. The oils are selected from among animal, vegetable, mineral or synthetic oils and in particular from liquid petrolatum, liquid paraffin, volatile or non-volatile silicone oils, isoparaffins, poly-α-olefins, or fluorinated and perfluorinated oils. Likewise, the waxes are advantageously selected from among animal, fossil, vegetable, mineral or synthetic waxes per se well known to this art.

Exemplary organic solvents include the lower alcohols and polyols.

The thickeners are advantageously selected from among crosslinked homopolymers of acrylic acid, or modified or unmodified guar gums and celluloses, such as hydroxypropylated guar gum, methylhydroxyethyl-cellulose, hydroxypropylmethyl cellulose, or hydroxyethylcellulose.

One skilled in this art will of course take care to select this or these optional additional compounds and/or the amounts thereof such that the advantageous properties, in particular the sun protection factors, intrinsically provided by the binary combination in accordance with the invention are not, or are not substantially, adversely affected by the envisaged addition or additions.

The compositions of the invention are easily formulated according to techniques well known to this art, in particular those suited for the formulation of emulsions of oil-in-water or water-in-oil type.

Such compositions can be provided, in particular, in the form of a simple or complex emulsion (O/W, W/O, O/W/O or W/O/W), such as a cream, a milk, a gel or a cream gel, a lotion, an ointment, a powder, or a solid tube or stick and can optionally be packaged as an aerosol and provided in the form of a foam or spray.

When formulated as an emsulsion, the aqueous phase thereof can comprise a non-ionic vesicular dispersion prepared according to known techniques (Bangham, Standish and Watkins, *J. Mol. Biol.,* 13, 238 (1965), FR-2,315,991 and FR-2,416,008).

The cosmetic compositions of the invention are useful; for protecting the human epidermis or the hair against ultraviolet rays, as an antisun/sunscreen composition or as a makeup product.

When the cosmetic compositions according to the invention are used for the photoprotection of the human epidermis against UV irradiation or as sunscreen compositions, they can be provided in the form of a suspension or dispersion in solvents or fatty substances, in the form of a non-ionic vesicular dispersion or in the form of an emulsion, preferably of oil-in-water type, such as a cream or a milk, in the form of an ointment, gel, cream gel, powder, solid tube, stick, aerosol foam or spray.

When the cosmetic compositions according to the invention are used for the photoprotection of the hair, they can be provided in the form of a shampoo, lotion, gel, emulsion or non-ionic vesicular dispersion and can constitute, for example, a rinse-out composition, to be applied before or after shampooing, before or after dyeing or bleaching and before, during or after permanent-waving or hair straightening, a styling or treating lotion or a styling or treating gel, a lotion or a gel for blow drying or hair setting, or a composition for permanent-waving or straightening, dyeing or bleaching the hair.

When the subject compositions are used as a product for making up the eyelashes, eyebrows or skin, such as a treatment cream for the epidermis, foundation, lipstick, eyeshadow, face powder, mascara or eyeliner, they can be provided in the anhydrous or aqueous, pasty or solid form, such as oil-in-water or water-in-oil emulsions, non-ionic vesicular dispersions, or suspensions.

For example, for the antisun/formulations in accordance with this invention which comprise a vehicle of oil-in-water emulsion type, the aqueous phase (comprising in particular the hydrophilic screening agents) generally constitutes from 50% to 95% by weight, preferably from 70% to 90% by weight, with respect to the total weight of the formulation, the oily phase (comprising in particular the lipophilic screening agents) from 5% to 50% by weight, preferably from 10% to 30% by weight, with respect to the total weight of the formulation, and the (co)emulsifier(s) from 0.5% to 20% by weight, preferably from 2% to 10% by weight, with respect to the total weight of the formulation.

As hereinbefore indicated, the present invention also features a regime/regimen for the cosmetic treatment of the skin or hair, to protect these against the deleterious effects of UV radiation, comprising topically applying onto the skin or hair, an effective amount of a subject cosmetic composition.

In order to further illustrate the present invention and the advantages thereof, the following specific examples are given, it being understood that same are intended only as illustrative and in nowise limitative.

In said examples to follow, all parts and percentages are given by weight.

The following three (3) compositions according to the invention were formulated via conventional cosmetic technique.

EXAMPLE 1

| COMPOSITION | Example 1 |
|---|---|
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{[4-(2-ethylhexyloxy)-2-hydroxy]-phenyl}-6-(4-methoxyphenyl)-1,3,5-triazine | 2 g |
| Glycerol | 15 g |
| Benzene-1,4-di(3-methylidene-10-camphorsulfonic acid) (Mexoryl SX-Chimex) | 2 g |
| Triethanolainine | q.s. pH 7 |
| Preservatives | q.s. |
| Demineralized water, q.s. for | 100 g |

EXAMPLE 2

| COMPOSITION | Example 2 |
| --- | --- |
| Glycerol mono/distearate/polyethylene glycol (100 EO) stearate mixture (Arlacel 165 FL, ICI) | 2 g |
| Stearyl alcohol (Lanette 18, Henkel) | 1 g |
| Palm oil stearic acid (Stearine TP, Stearinerie Dubois) | 2.5 g |
| Polydimethylsiloxane (Dow Corning 200 Fluid, Dow Corning) | 0.5 g |
| Benzoate of $C_{12}/C_{15}$ alcohols (Witconol TN, Witco) | 20 g |
| Triethanolamine | 0.5 g |
| 2,4-Bis{[4-(tris(trimethylsiloxy)silyl-propyloxy)-2-hydroxy]phenyl}-6-(4-methoxy-phenyl)-1,3,5-triazine | 2.5 g |
| Propylene glycol | 4 g |
| Glycerol | 4 g |
| Benzene-1,4-di(3-methylidene-10 camphorsulfonic acid) (Mexoryl SX-Chimex) | 2.5 g |
| Hexadecyl phosphate, potassium salt (Amphisol K, Hoffman-Laroche) | 1 g |
| Triethanolamine | q.s. pH 7 |
| Polyacrylic acid (Synthalen K, 3V) | 0.3 g |
| Hydroxypropyl methyl cellulose (Methocel F4M, Dow Chemical) | 0.1 g |
| Preservatives | q. s. |
| Demineralized water, q.s. for | 100 g |

EXAMPLE 3

| COMPOSITION | Example 3 |
| --- | --- |
| 80/20 Mixture of cetearyl alcohol and of oxyethylenated (33 EO) cetearyl alcohol (Sinnowax AO, Renkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{[4-(1',1',1',3',5',5',5'-hepta methyltrisiloxy-2"-methylpropyloxy)-2-hydroxy]phenyl}-6-(4-methoxyphenyl)-1,3,5-triazine | 2 g |
| Glycerol | 15 g |
| Benzene-1,4-di(3-methylidene-10-camphorsulfonic acid) (Mexoryl SX-Chimex) | 2 g |
| Triethanolamine | q.s. pH 7 |
| Preservatives | q. s. |
| Demineralized water, g.s. for | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising synergistically UV-photoprotecting effective amounts of each of (i) benzene-1,4-di(3-methylidene-10-camphorsulfonic acid), or partially or completely neutralized form thereof, and (ii) at least one bisresorcinyltriazine compound having the structural formula:

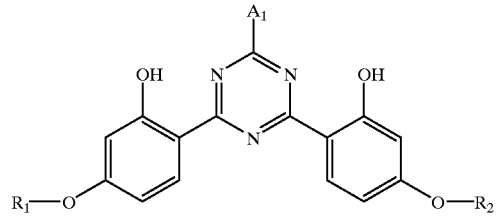

(II)

in which the $R_1$ and $R_2$ radicals, which may be identical or different, are each a $C_3$–$C_{18}$ alkyl radical, a $C_2$–$C_{18}$ alkenyl radical, or a residue of formula —$CH_2$—$CH(OH)$—$CH_2$—$OT_1$ wherein $T_1$ is a hydrogen atom or a $C_1$–$C_8$ alkyl radical; with the proviso that the $R_1$ and $R_2$ radicals, which again may be identical or different, can also be a residue having the following formula (1):

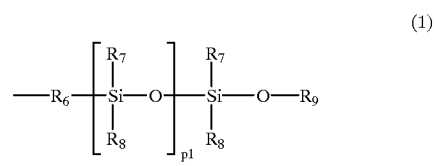

(1)

in which $R_6$ is a covalent bond, a linear or branched $C_1$–$C_4$ alkyl radical, or a residue of formula —$C_{m1}H_{2m1}$— or —$C_{m1}H_{2m1}$—O— wherein $m_1$ is a number ranging from 1 to 4; $p_1$ is a number ranging from 0 to 5; and the $R_7$, $R_8$ and $R_9$ radicals, which may be identical or different, are each a $C_1$–$C_{18}$ alkyl radical, a $C_1$–$C_{18}$ alkoxy radical, or a residue having the formula:

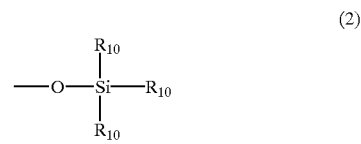

(2)

wherein $R_{10}$ is a $C_1$–$C_5$ alkyl radical; and $A_1$ is a residue having one of the following formulae:

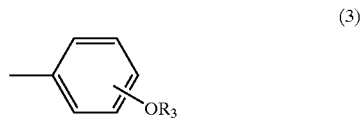

(3)

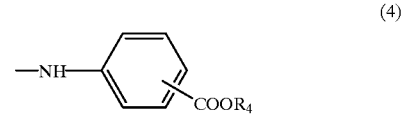

(4)

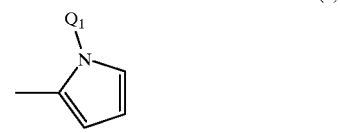

(5)

in which $R_3$ is a hydrogen atom, a $C_1$–$C_{10}$ alkyl radical, a radical of the formula —$(CH_2CHR_5$—$O)_{n1}R_4$ wherein $n_1$ is a number ranging from 1 to 16 and $R_5$ is a hydrogen atom or methyl radical, or a residue having the formula —$CH_2$—

CH(OH)—CH$_2$OT$_1$ wherein T$_1$ is as defined above; R$_4$ is a hydrogen atom, a metal cation M, a C$_1$–C$_5$ alkyl radical, or a residue of formula —(CH$_2$)$_{m2}$—OT$_1$, wherein m$_2$ is a number ranging from 1 to 4 and T$_1$ is as defined above; and Q$_1$ is a C$_1$–C$_{18}$ alkyl radical, formulated into a topically applicable, cosmetically acceptable vehicle, diluent or carrier thereof.

2. The sunscreen/cosmetic composition as defined by claim 1, said at least one bisresorcinyltriazine compound (II) comprising 2,4-bis{[4-(2-ethylhexyloxy)-2-hydroxy]phenyl}-6-(4-methoxyphenyl)-1,3,5-triazine; 2,4-bis{[4-(3-(2-propyloxy)-2-hydroxypropyloxy)2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethyloxycarbonyl)phenylamino]-1,3,5-triazine; 2,4-bis{[4-(tris(trimethylsiloxy)silylpropyloxy)-2-hydroxy]phenyl}-6-(4-methoxyphenyl)-1,3,5-triazine; 2,4-bis{[4-(2"-methylpropenyloxy)-2-hydroxy]phenyl}-6-(4-methoxyphenyl)-1,3,5-triazine; 2,4-bis{[4-(1',1',1',3',5',5',5'-heptamethyltri-siloxy-2"-methylpropyloxy)-2-hydroxy]phenyl}-6-(4-methoxyphenyl)-1,3,5-triazine; 2,4-bis{[4-(3-(2-propyloxy)-2-hydroxypropyloxy)-2-hydroxy]phenyl}-6-[4-(ethoxycarbonyl)phenylamino]-1,3,5-triazine; or 2,4-bis{[4-(2-ethylhexyloxy)-2-hydroxy]phenyl}-6-(1-methylpyrrol-2-yl)-1,3,5-triazine.

3. The sunscreen/cosmetic composition as defined by claim 2, said at least one bisresorcinyltriazine compound (II) comprising 2,4-bis{[4-(2-ethylhexyloxy)-2-hydroxy]phenyl}-6-(4-methoxyphenyl)-1,3,5-triazine; 2,4-bis{[4-(tris(trimethylsiloxy)silylpropyloxy)-2-hydroxy]phenyl}-6-(4-methoxyphenyl)-1,3,5-triazine; or 2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

4. The sunscreen/cosmetic composition as defined by claim 1, comprising from 0.1% to 15% by weight of said at least one bisresorcinyltriazine compound.

5. The sunscreen/cosmetic composition as defined by claim 4, comprising from 0.2% to 10% by weight of said at least one bisresorcinyltriazine compound.

6. The sunscreen/cosmetic composition as defined by claim 1, said benzene-1,4-di(3-methylidene-10-camphorsulfonic acid) or neutralized form thereof having the following formula (I):

7. The sunscreen/cosmetic composition as defined by claim 6, comprising from about 0.1% to 15% by weight of said benzene-1,4-di(3-methylidene-10-camphorsulfonic acid) or neutralized form thereof.

8. The sunscreen/cosmetic composition as defined by claim 7, comprising from about 0.2% to 10% by weight of said benzene-1,4-di(3-methylidene-10-camphorsulfonic acid) or neutralized form thereof.

9. The sunscreen/cosmetic composition as defined by claim 6, wherein formula (I) M$^{n+}$ is Ca$^{2+}$, Zn$^{2+}$, Mg$^{2+}$, Ba$^{2+}$, Al$^{3+}$ or Zr$^{4+}$.

10. The sunscreen/cosmetic composition as defined by claim 1, formulated as an oil-in-water emulsion.

11. The sunscreen/cosmetic composition as defined by claim 1, formulated as a water-in-oil emulsion.

12. The sunscreen/cosmetic composition as defined by claim 1, further comprising at least one additional hydrophilic or lipophilic organic UV-A and/or UV-B sunscreen.

13. The sunscreen/cosmetic composition as defined by claim 12, further comprising at least one cinnamic derivative, salicylic derivative, camphor derivative, triazine derivative, benzophenone derivative, benzimidazole derivative, β-β-diphenylacrylate derivative, p-aminobenzoic acid derivative, sunscreen polymer, or sunscreen silicone.

14. The sunscreen/cosmetic composition as defined by claim 1, further comprising a photoprotecting effective amount of particulates of at least one coated or uncoated inorganic pigment or nanopigment.

15. The sunscreen/cosmetic composition as defined by claim 14, said at least one pigment or nanopigment comprising titanium dioxide, zinc oxide, iron oxide, zirconium oxide, cerium oxide, or mixture thereof.

16. The sunscreen/cosmetic composition as defined by claim 1, further comprising at least one active agent for the artificial tanning and/or browning of human skin.

17. The sunscreen/cosmetic composition as defined by claim 1, further comprising at least one cosmetically acceptable adjuvant or additive.

18. The sunscreen/cosmetic composition as defined by claim 17, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

19. The sunscreen/cosmetic composition as defined by claim 1, comprising a nonionic vesicle dispersion, emulsion, cream, milk, gel, cream gel, ointment, suspension, dispersion, powder, solid stick or tube, foam or spray.

(I)

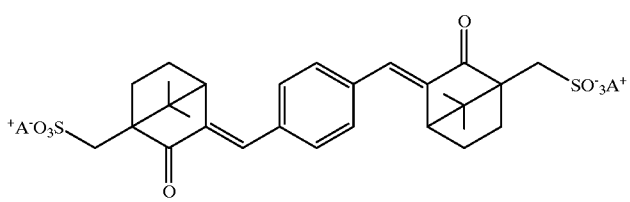

in which A is a hydrogen atom, an alkali metal or an NH(R)$_3^+$ radical, wherein the R radicals, which may be identical or different, are each a hydrogen atom, a C$_1$–C$_4$ alkyl or hydroxyalkyl radical, or an M$^{n+}$/n group, wherein M$^{n+}$ is a polyvalent metal cation in which n is equal to 2, 3 or 4.

20. The sunscreen/cosmetic composition as defined by claim 1, comprising a makeup.

21. The sunscreen/cosmetic composition as defined by claim 20, comprising an anhydrous or aqueous solid or paste, emulsion, suspension, or dispersion.

22. The sunscreen/cosmetic composition as defined by claim 1, comprising a shampoo, lotion, gel, nonionic vesicle dispersion, hair lacquer, or rinse.

23. The sunscreen/cosmetic composition as defined by claim 1, having a sun protection factor of at least 2.

24. A regime/regimen for protecting human skin and/or hair against the deleterious effects of ultraviolet irradiation, comprising topically applying thereto an effective amount of the sunscreen/cosmetic composition as defined by claim 1.

25. A regime/regimen for protecting human skin and/or hair against the deleterious effects of solar radiation, comprising topically applying thereto an effective amount of the sunscreen/cosmetic composition as defined by claim 1.

\* \* \* \* \*